US012659657B2

(12) United States Patent
Sellers

(10) Patent No.: US 12,659,657 B2
(45) Date of Patent: Jun. 16, 2026

(54) HEARING PROTECTION APPARATUS

(71) Applicant: Corey Sellers, Monticello, AR (US)

(72) Inventor: Corey Sellers, Monticello, AR (US)

( * ) Notice: Subject to any disclaimer, the term of this patent is extended or adjusted under 35 U.S.C. 154(b) by 296 days.

(21) Appl. No.: 18/209,746

(22) Filed: Jun. 14, 2023

(65) Prior Publication Data

US 2024/0422477 A1 Dec. 19, 2024

(51) Int. Cl.
*H04R 3/00* (2006.01)
*A61F 11/14* (2006.01)
*H04K 3/00* (2006.01)

(52) U.S. Cl.
CPC ............ *H04R 3/007* (2013.01); *A61F 11/145* (2022.01); *H04K 3/42* (2013.01)

(58) Field of Classification Search
CPC ............ H04R 3/007; A61F 11/14; H04K 3/42
USPC ...................................... 381/73.1, 72; 455/1
See application file for complete search history.

(56) References Cited

U.S. PATENT DOCUMENTS

| | | | |
|---|---|---|---|
| 2,314,782 A | | 3/1943 | Goretsky |
| 5,241,971 A | | 9/1993 | Lundin |
| D434,191 S | | 11/2000 | Emilsson |
| 6,151,717 A | * | 11/2000 | Lindgren ................ A61F 11/14 |
| | | | 181/129 |
| 6,678,897 B2 | | 1/2004 | Lindgren |
| 2006/0015989 A1 | | 1/2006 | Faussett |
| 2013/0303075 A1 | * | 11/2013 | Smiley ................... H04K 3/415 |
| | | | 455/1 |
| 2015/0365760 A1 | * | 12/2015 | Jiang .................... H04R 1/1083 |
| | | | 381/71.6 |
| 2019/0103940 A1 | * | 4/2019 | Kundu .................... H04W 4/80 |

FOREIGN PATENT DOCUMENTS

CA          2378139          1/2001

* cited by examiner

*Primary Examiner* — Vivian C Chin
*Assistant Examiner* — Con P Tran

(57) ABSTRACT

A hearing protection apparatus for disrupting wireless transmissions near the ears of a user while protecting the ears from noise includes an ear covering assembly comprising a headband and a pair of cups which is positionable to cover the ears of a user. A jammer circuit is provided which transmits a jamming signal toward the ears of the user to disrupt wireless communication near the ears of the user.

1 Claim, 5 Drawing Sheets

HEARING PROTECTION APPARATUS

BACKGROUND OF THE INVENTION

(1) Field of the Invention

The disclosure relates to hearing protection devices and more particularly pertains to a new hearing protection device for disrupting wireless transmissions near the ears of a user while protecting the ears from noise.

(2) Description of Related Art Including Information Disclosed Under 37 CFR 1.97 and 1.98

People working in loud environments typically wear a hearing protection device to prevent hearing damage to their ears. In some situations, the users of the hearing protection devices want to listen to audio files or streams while wearing the hearing protection device, so the users place wireless earphones in their ears underneath the hearing protection device. However, this is often a dangerous practice, because plugging ears with earphones, playing audio into the ears, and covering the ears with a hearing protection device can limit the user's aural perception of his or her environment to an extent that the user cannot hear sounds indicating impending harm to the user. This is especially true in particularly dangerous areas like manufacturing facilities, construction sites, and the like.

The prior art has described hearing protection devices which facilitate monitoring a user of a hearing protection device to ensure the user is not engaging in this dangerous practice. This includes, for example, a hearing protection device with translucent portions facilitating the viewing of an object in the user's ear. However, the prior art does not disclose a hearing protection apparatus which transmits a jamming signal to disrupt wireless communication near the user's ears. Such a device would be desirable, because instead of requiring visual identification of a wireless earphone in the user's ear, the wireless earphone could simply be prevented from receiving wireless signals necessary to play audio into the user's ears. Thus, the user will not be able to listen to the audio as desired by the user, and there is therefore no incentive for the user to place the earphones in his or her ears.

BRIEF SUMMARY OF THE INVENTION

An embodiment of the disclosure meets the needs presented above by generally comprising an ear covering assembly comprising a headband, a first cup, and a second cup. The headband is configured to be positioned to extend over a head of a user. The first and second cups are coupled to a first end and a second end of the headband respectively and are configured to be positioned over a first ear and a second ear of the user respectively. The first and second cups attenuate sound directed at the user. A housing is coupled to the ear covering assembly, and a control circuit is coupled to and positioned in the housing. A jammer circuit is electrically coupled to the control circuit and is configured to output a jamming signal toward each of the first and second ears of the user to disrupt wireless communication near each of the first and second ears.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
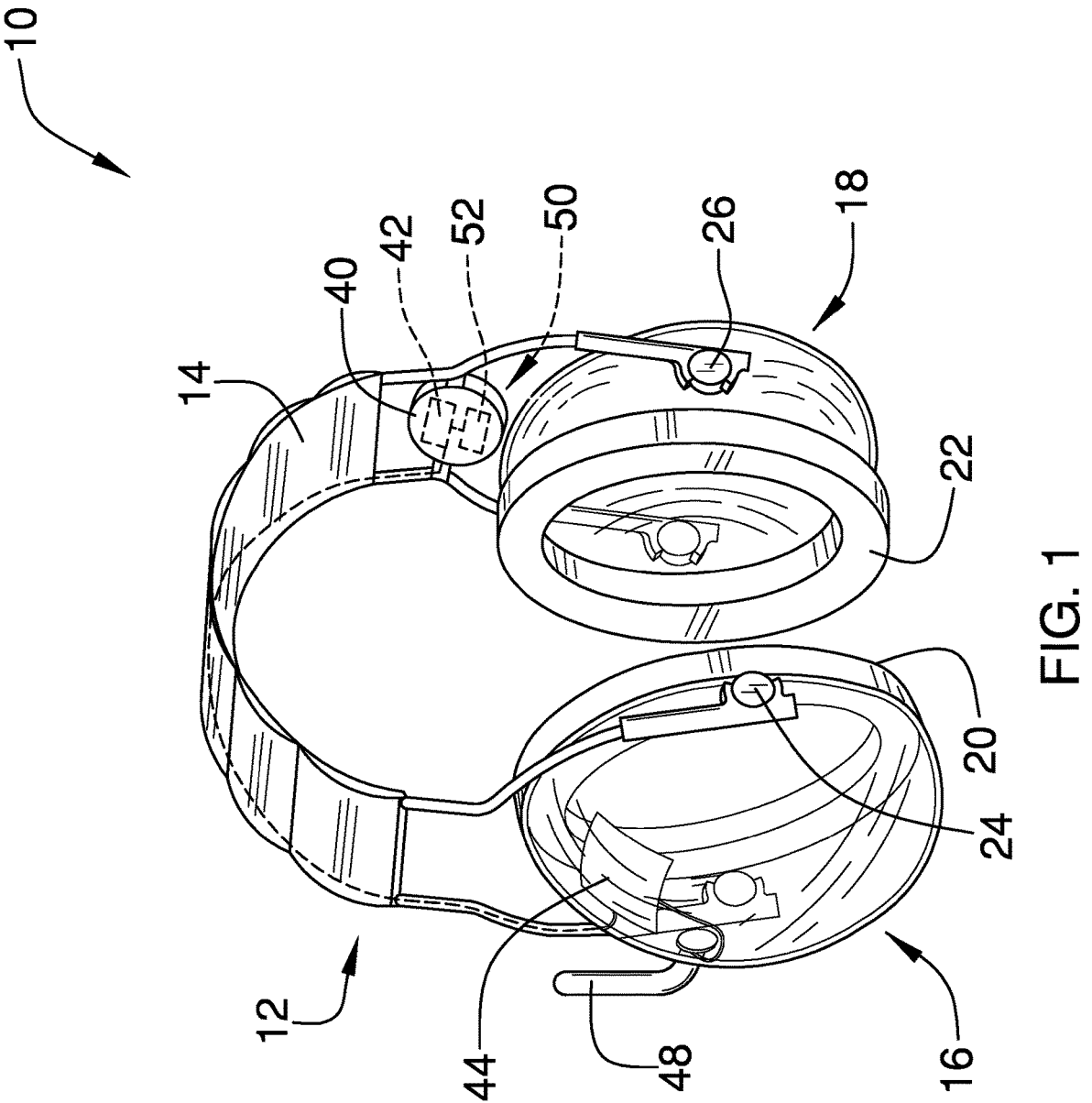
FIG. 1 is a perspective view of a hearing protection apparatus according to an embodiment of the disclosure.
Figures 2, 3:
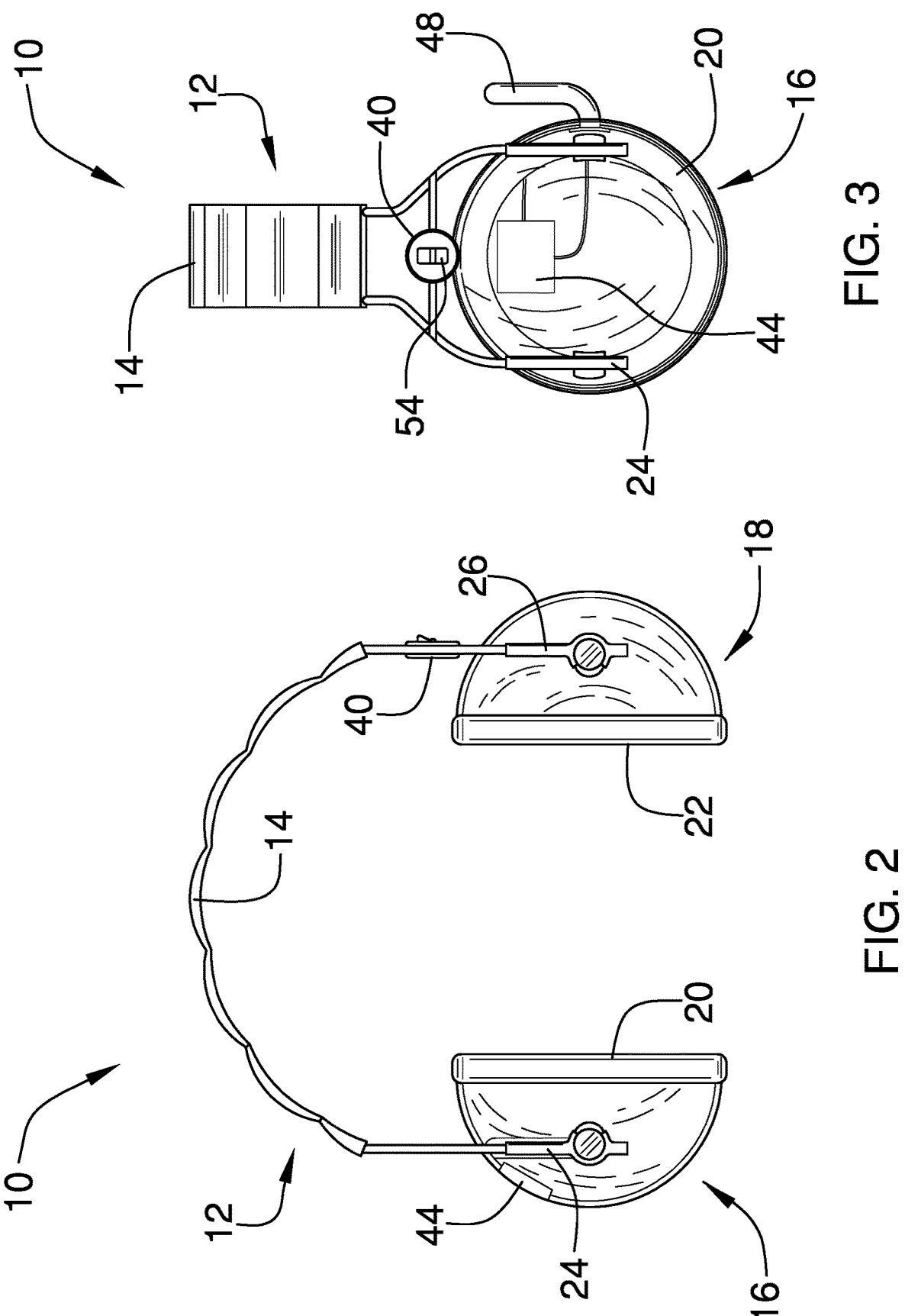
FIG. 2 is a front view of an embodiment of the disclosure.
FIG. 3 is a side view of an embodiment of the disclosure.
Figure 4:
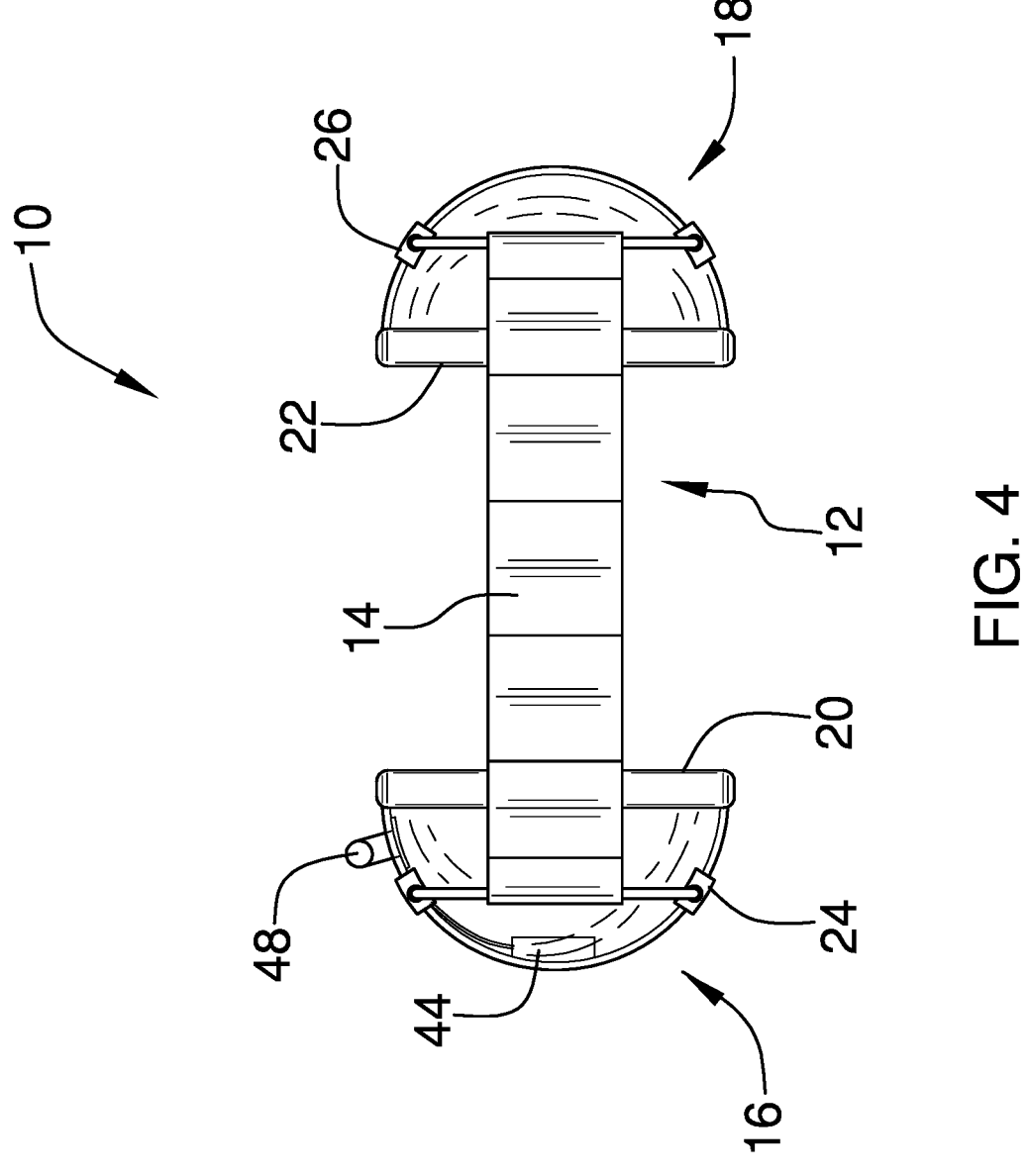
FIG. 4 is a top view of an embodiment of the disclosure.
Figure 5:
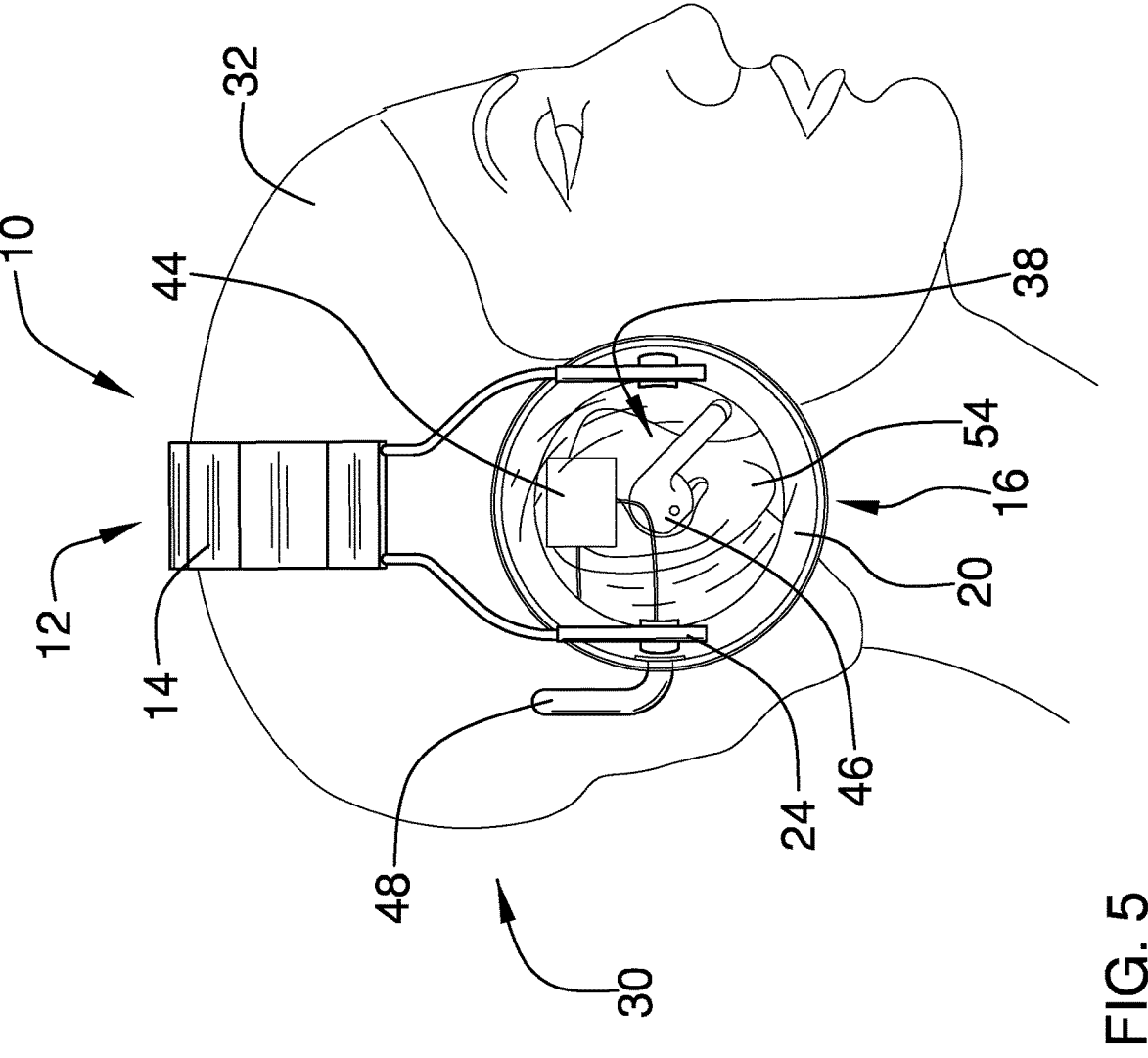
FIG. 5 is an in-use view of an embodiment of the disclosure.
Figure 6:
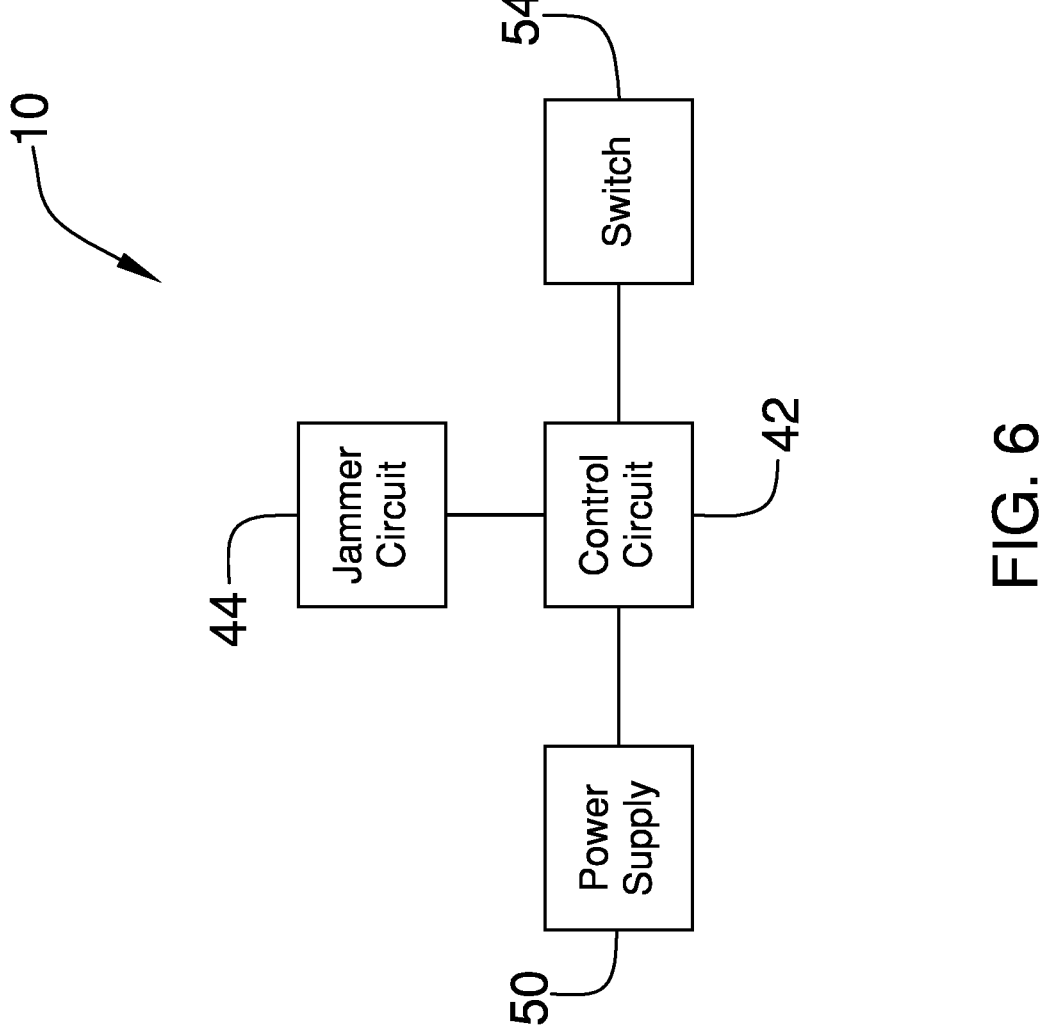
FIG. 6 is a block diagram of an embodiment of the disclosure.

With reference now to the drawings, and in particular to FIGS. 1 through 6 thereof, a new hearing protection device embodying the principles and concepts of an embodiment of the disclosure and generally designated by the reference numeral 10 will be described.

As best illustrated in FIGS. 1 through 6, the hearing protection apparatus 10 generally comprises an ear covering assembly 12 comprising a headband 14, a first cup 16, a second cup 18, a first cushion 20, and a second cushion 22. The headband 14 is configured for being positioned to extend over a head 32 of a user 30. The first and second cups 16, 18 are coupled to a first end 24 and a second end 26 of the headband 14 respectively and are configured to be positioned over a first ear 34 and a second ear (not shown) respectively. The first and second cups 16, 18 attenuate sound directed at the user 30. At least a portion of each of the first and second cups 16, 18 is translucent to facilitate viewing of an object 38 in the first or second ear of the user 30. The first and second cushion 20, 22 are coupled to and extend along a first rim of the first cup 16 and a second rim of the second cup 18 respectively. Each one of the first and second cushion 20, 22 is resiliently and compressively flexible to facilitate the formation of a seal with the head 32 and around the first ear 34 and second ear respectively.

A housing 40 is coupled to the ear covering assembly 12 and is positioned on the headband 14 adjacent to the first cup 16. A control circuit 42 is coupled to and positioned in the housing 40. A jammer circuit 44 is electrically coupled to the control circuit 42 and is configured to output a jamming signal toward each of the first ear 34 and second ear of the user 30 to disrupt wireless communication near each of the first ear 34 and second ear. The jammer circuit 44 emits a jamming signal comprising a radio wave with a frequency of between 2400.0 megahertz and 2483.5 megahertz such that devices using the Bluetooth communication standard, such as wireless earphones 46, will be disrupted by the jamming signal. The jammer circuit 44 is embedded in the first cup 16 of the ear covering assembly 12 and includes an antenna 48 protruding away from the first cup 16.

A power supply 50 is electrically coupled to the control circuit 42 and is positioned in the housing 40. The power supply 50 comprises a battery 52. A power switch 54 is electrically coupled to the control circuit 42 and is actuatable to activate the jammer circuit 44. The power switch 54 is positioned on the housing 40. In some embodiments, the jammer circuit 44 is actuatable remotely. In other embodiments, the power switch 54 may be protected to prevent tampering.

In use, the user 30 wears the ear covering assembly 12 with the first and second cups 16, 18 positioned over the first ear 34 and second ear respectively to protect the user's 30 first ear 34 and second ear from hearing damage. The power switch 54 is then activated to activate the jammer circuit 44 to emit the jamming signal, thus disrupting radio wave transmissions being transmitted to earphones 46 or other devices near the first ear 34 and second ear of the user 30.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

4

I claim:

1. A hearing protection apparatus comprising:
an ear covering assembly comprising:
   a headband being configured to be positioned to extend over a head of a user;
   a first cup and a second cup, the first cup configured for being positioned over a first ear of the user and being coupled to a first end of the headband, the second cup configured for being positioned over a second ear of the user and being coupled to a second end of the headband, the first and second cups attenuating sound directed at the user, at least a portion of each of the first and second cups being translucent to facilitate viewing of an object in the first or second ear of the user; and
   a first cushion and a second cushion, the first cushion being coupled to and extending along a first rim of the first cup, the second cushion being coupled to and extending along a second rim of the second cup, each of the first and second cushions being resiliently and compressively flexible to facilitate a formation of a seal with the head and around each of the first and second ears;
a housing being coupled to the ear covering assembly, the housing being positioned on the headband adjacent to the first cup;
a control circuit being coupled to and positioned in the housing;
a jammer circuit being electrically coupled to the control circuit and being configured to output a jamming signal toward each of the first and second ears of the user to disrupt wireless communication near each of the first and second ears, the jammer circuit emitting the jamming signal comprising a radio wave with a frequency of between 2400.0 megahertz and 2483.5 megahertz, the jammer circuit being embedded in the first cup of the ear covering assembly, the jammer circuit including an antenna protruding away from the first cup;
a power supply being electrically coupled to the control circuit, the power supply being positioned in the housing, the power supply comprising a battery; and
a power switch being electrically coupled to the control circuit, the power switch being actuatable to activate the jammer circuit, the power switch being positioned on the housing.

* * * * *